United States Patent [19]
Herweck et al.

[11] Patent Number: 6,010,529
[45] Date of Patent: Jan. 4, 2000

[54] EXPANDABLE SHIELDED VESSEL SUPPORT

[75] Inventors: Steve A. Herweck, Nashua, N.H.; Peter Gingras, Bedford, Mass.; Paul Martakos, Pelham; Theodore Karwoski, Hudson, both of N.H.

[73] Assignee: Atrium Medical Corporation, Hudson, N.H.

[21] Appl. No.: 08/759,877

[22] Filed: Dec. 3, 1996

[51] Int. Cl.[7] .................................. A61F 2/06; A61F 2/04
[52] U.S. Cl. .................................. 623/1; 623/11; 623/12; 606/192; 606/194; 606/195; 606/198; 600/36
[58] Field of Search .................................. 623/1, 11, 12; 606/192, 194, 195, 198; 600/36

[56] References Cited

U.S. PATENT DOCUMENTS

| | | | |
|---|---|---|---|
| Re. 31,618 | 7/1984 | Mano et al. | 3/1.4 |
| 3,105,492 | 10/1963 | Jeckel | 128/334 |
| 3,479,670 | 11/1969 | Medell | 128/334 |
| 3,993,078 | 11/1976 | Bergentz | 128/334 |

(List continued on next page.)

FOREIGN PATENT DOCUMENTS

| | | |
|---|---|---|
| 0233102 | 1/1987 | European Pat. Off. . |
| 0269449 | 1/1988 | European Pat. Off. . |
| 0256748 | 2/1988 | European Pat. Off. . |
| 0605243 | 6/1994 | European Pat. Off. . |

(List continued on next page.)

OTHER PUBLICATIONS

Bergeron et al., "Tensile Characteristics of Expanded PTFE for use in Endoluminal Grafting" *Journal of Endovascular Surgery*, vol. 2, 202–203 (1995).

Edelman et al., "Hoop Dreams: Stents Without Restenosis" *Circulation*, vol. 94 No. 6, 1199–1202 (1996).

Distat Brochure, 3 Pages, Gore Technologies Worldwide.

Marin et al., "Stented Grafts for the Treatment of Arterial Vascular Disease" *Surgical Technology International III*, 421–429.

*Primary Examiner*—Mickey Yu
*Assistant Examiner*—Choon P. Koh
*Attorney, Agent, or Firm*—Lahive & Cockfield, LLP

[57] ABSTRACT

A radially expandable support body is enveloped within a cocoon. In a preferred construction, the support is a stent, and a tube of polymeric material, e.g. polytetrafluoroethylene (PTFE), passes through the interior of the stent body and is turned back upon itself over the stent to form a cuff. The assembly is then heated and the outer layer contacts and coalesces with the inner layer, closely surrounding the stent body within a folded envelope having a continuous and seamless end. In one embodiment, an end portion of the tube is expanded before folding back over the stent. The end portion, which becomes an exterior surface of the finished product, thus acquires a greater degree of porosity. Each end of the central tube may be so expanded, and folded back to seal all surfaces and both ends. The stent body itself may be a ring, or a short series of spaced-apart rings, or a wire or web, or a sheet possessing a number of apertures extending entirely through the sheet. The spaces or apertures are covered over or bridged by both the inner and outer polymer layers. The apertures, which may comprise under five to over eighty percent of the surface area of the stent, constitute regions or a grid of points through which the material is coalesced and continuously bonded, and around which strain is distributed by the support. These points or regions remain tacked together so expansion of the assembly does not delaminate the polymer or create flaps and pockets. In another embodiment, a two tube construction is cuffed and assembled into a similarly unitized and seamless stent. One tube is cuffed back, and the other tube covers the cuffed stent. In this embodiment both the tube thicknesses and porosities may differ substantially. For example the inner porosity may be selected to enhance blood flow or intimal regeneration, and the outer surface may have a porosity to encourage anchoring to external muscle tissue.

31 Claims, 6 Drawing Sheets

U.S. PATENT DOCUMENTS

| | | | |
|---|---|---|---|
| 4,130,904 | 12/1978 | Whalen | 3/1.4 |
| 4,193,138 | 3/1980 | Okita | 3/1.4 |
| 4,208,745 | 6/1980 | Okita | 3/1.4 |
| 4,234,535 | 11/1980 | Okita | 264/519 |
| 4,321,711 | 3/1982 | Mano | 3/1.4 |
| 4,550,447 | 11/1985 | Seiler et al. | 623/1 |
| 4,629,458 | 12/1986 | Pinchuk | 623/1 |
| 4,647,416 | 3/1987 | Seiler et al. | 264/118 |
| 4,731,073 | 3/1988 | Robinson | 623/1 |
| 4,816,339 | 3/1989 | Tu et al. | 428/421 |
| 4,955,899 | 9/1990 | Della Corna et al. | 623/1 |
| 5,028,597 | 7/1991 | Kodama et al. | 514/56 |
| 5,061,276 | 10/1991 | Tu et al. | 623/1 |
| 5,064,593 | 11/1991 | Tamaru et al. | 264/113 |
| 5,123,917 | 6/1992 | Lee | 623/1 |
| 5,152,782 | 10/1992 | Kowligi et al. | 623/1 |
| 5,163,951 | 11/1992 | Pinchuk et al. | 623/1 |
| 5,192,310 | 3/1993 | Herweck et al. | 623/1 |
| 5,197,976 | 3/1993 | Herweck et al. | 623/1 |
| 5,217,666 | 6/1993 | Tamaru et al. | 264/112 |
| 5,225,131 | 7/1993 | Tamaru et al. | 264/113 |
| 5,229,045 | 7/1993 | Soldani | 264/41 |
| 5,234,739 | 8/1993 | Tanaru et al. | 428/131 |
| 5,282,847 | 2/1994 | Trescony et al. | 623/1 |
| 5,282,860 | 2/1994 | Matsuno et al. | 623/12 |
| 5,320,100 | 6/1994 | Herweck et al. | 128/654 |
| 5,354,329 | 10/1994 | Whalen | 623/1 |
| 5,389,106 | 2/1995 | Tower | 623/1 |
| 5,411,550 | 5/1995 | Herweck et al. | 623/1 |
| 5,413,597 | 5/1995 | Krajicek | 623/1 |
| 5,433,909 | 7/1995 | Martakos et al. | 264/209 |
| 5,453,278 | 9/1995 | Chan et al. | 424/422 |
| 5,512,360 | 4/1996 | King | 428/304.4 |
| 5,522,881 | 6/1996 | Lentz | 623/1 |
| 5,527,353 | 6/1996 | Schmitt | 623/1 |
| 5,534,287 | 7/1996 | Lukic | 427/2.25 |
| 5,549,663 | 8/1996 | Cottone, Jr. | 623/1 |
| 5,556,414 | 9/1996 | Turi | 606/198 |
| 5,556,426 | 9/1996 | Popadiuk et al. | 623/1 |
| 5,571,169 | 11/1996 | Plaia et al. | 623/1 |
| 5,571,173 | 11/1996 | Parodi | 623/1 |
| 5,607,478 | 3/1997 | Lentz et al. | 623/12 |
| 5,628,788 | 5/1997 | Pinchuk | 623/1 |
| 5,667,523 | 9/1997 | Bynon et al. | 623/1 |
| 5,674,241 | 10/1997 | Bley et al. | 623/1 |
| 5,683,451 | 11/1997 | Lenker et al. | 623/12 |
| 5,700,285 | 12/1997 | Myers et al. | 623/1 |
| 5,718,973 | 2/1998 | Lewis et al. | 623/12 |
| 5,735,892 | 4/1998 | Myers et al. | 606/198 |
| 5,741,324 | 4/1998 | Glastra | 623/1 |
| 5,755,770 | 5/1998 | Ravenscroft | 623/1 |
| 5,755,774 | 5/1998 | Pinchuk | 623/1 |
| 5,769,882 | 6/1998 | Fogarty et al. | 623/1 |

FOREIGN PATENT DOCUMENTS

| | | |
|---|---|---|
| 2248015 | 5/1975 | France . |
| 3918736 | 12/1990 | Germany . |
| 95/05132 | 2/1995 | WIPO . |
| 95/05277 | 2/1995 | WIPO . |
| 95/05555 | 2/1995 | WIPO . |
| 96/00103 | 1/1996 | WIPO . |
| 96/28115 | 9/1996 | WIPO . |

EXPANDABLE SHIELDED VESSEL SUPPORT

REFERENCE TO RELATED PATENTS AND PATENT APPLICATIONS

This application relates to the commonly owned United States Patent Applications having the following titles and attorney docket numbers, which are being filed by applicant of even date herewith: VASCULAR ENDOPROSTHESIS AND METHOD, Attorney Docket ATA-127; MULTI-STAGE PROSTHESIS, Attorney Docket ATA-140; and PROSTHESIS WITH IN-WALL MODULATION, Attorney Docket ATA-142. It also relates to applicants' earlier U.S. Pat. Nos. 5,433,909 and 5,474,824. The foregoing patents describe methods of making extruded PTFE material having large oriented nodes, uniaxially oriented fibrils and a pore structure of oriented channels that differs at different surfaces, or that varies along the thickness dimension. The aforesaid patent applications each describe constructions or methods of use for prostheses, which are further useful in the embodiments and applications of the present invention. Each of the aforementioned United States Patents and Patent Applications is hereby incorporated by reference herein in its entirety.

BACKGROUND

The present invention relates to vessels and vascular support structures, such as stays, stents and support rings which are used for maintaining open a biological passage, such as an artery. A great many constructions for both prostheses and stents are known in the art, ranging from simple wire or plastic rings and arrangements of stiff but flexible sheets or shells, to technologically advanced constructions wherein a wire structure of heat memory alloy flips to an enlarged memory configuration, or wherein a solid tubular body is fabricated with microscopically thin laser-cut slots which convert the solid cylinder into an expandable body that opens out to form a mesh-like but reasonably stiff surface support. One commercial embodiment of this latter type of stent, referred to as the Palmaz stent after the surgeon who popularized this construction, is in common use now. Another common form of stent consists of wire crimped into a zig zag pattern which can be expanded to attain a much larger length or diameter. Stents of this form may be formed as individual rings, or serpentine windings, or as pairs of helical windings which act against each other to counterbalance twist while expanding radially. Numerous other constructions are known.

Many if not all of the materials used for stents involve metal or carbon fiber materials which are highly electropositive and are bio-active. Since stents tend to be used under conditions were they are counteracting disease processes, supporting healing processes, or guarding against stenosis of a passage, bio-activity, which may encourage undesirable or poorly regulated growth processes, or lead to clot formation, should be avoided. Coating of the stent can keep the stent from directly contacting surrounding tissue or fluids, and thus can theoretically protect against unwanted electrochemically induced tissue reactions.

In the field of expandable stents, however, a further problem arises due to the fact that many effective or compact stent constructions involve filamentous or wire-like structures which have numerous apertures or spaces between the various strands or structural elements of the stent. With these constructions, tissue may grow through the openings of the stent. Furthermore, the stent itself may provoke a foreign body reaction and be both a stimulus for and a framework supporting, proliferative tissue growth, resulting, for example, in scar tissue or restenosis of the very region it is placed to control.

One approach to this drawback is to provide a coating, liner or cover for the stent which prevents the healing or diseased layer of tissue from directly contacting the stent or from passing through the stent in any way. Such liners may be formed, for example, of porous polytetrafluoroethylene (PTFE) which allows the passage of fluids and vital materials while serving as a barrier to tissue growth. However, when applying such a construction, a further difficulty which may arise is that the layer or sleeve of polymer must be attached to the stent for example, by staples or sutures at one end, or is prone to developing loose pockets or folds which might accumulate organic matter or lead to sepsis or unusual growth. Also, the necessarily thin liner material may detach or degrade. The risk of loose or unattached liner material is particularly great for constructions which utilize poorly adherent polymers, such as PTFE, or structures which seek to combine an expandable stent of stiff material, which changes both its dimension and its shape, with a dissimilar liner or shell.

Accordingly, there remains a need for a covered support construction of enhanced hardiness and implant compatibility.

There is also a need for an expandable vessel support which forms a unitized and non-delaminating tissue barrier.

There is also a need for a need for vascular liner having atraumatic properties and haemodynamic shape.

SUMMARY OF THE INVENTION

These and other objects are attained in a support according to the present invention wherein a radially expandable support body is enclosed within a solid but expandable polymer body of porous and expanded PTFE material that physically isolates the support body from surrounding blood and tissue.

In one preferred construction, the support body is a stent that is cocooned within a cuffed sheet. In this construction, the sheet is originally a tube of polytetrafluoroethylene (PTFE) material, which passes through the interior of the stent and is cuffed, e.g., is folded back upon itself, over the stent, in manner similar to the folding of a sock, so that the folded-back end of the tube becomes an outer layer smoothly extending around the end and covering the outside of the stent. The assembly is then heated, causing the outer layer to shrink and coalesce with the inner layer so that the stent is enclosed within a folded envelope having a continuous and seamless end portion. Preferably, radial pressure is applied during the heating so that the layers conform tightly to the support body and fill all interstitial spaces thereof. In other constructions, support members lie within pockets extending in the direction of expansile deformation.

Preferably, the tube is porous PTFE, having a microstructure of fibrous material interconnecting nodes of solid polymer, and the PTFE forms a soft and pliant surface that cushions the edges of the support body, or stent, and blocks direct contact between the stent and surrounding tissue, so that any fluids or material must penetrate the mat of fibrils to contact the stent environment. By first expanding and end portion of the tube before folding it back over the stent, the end portion, which becomes an exterior surface of the finished product, may be provided with a degree of porosity which is greater than that of the interior surface. In a further embodiment, each end of the central tube is so expanded, and then folded back so that the assembly is closed over at both ends and has a single seam extending circumferentially around the outside where one end meets or overlaps a portion of the other end of the tube part way along the body of the assembly. Alternatively, the outer surface may be covered by a wrap, or by a separate polymer tube; in this case the inner tube may have a relatively short end cuff portion, which is preferably folded over the outer cover for a short distance.

In a preferred embodiment, the entire inner and outer portions are formed of a single PTFE tube and are heated to both shrink the tube down into a compact and thin film-like cocoon, and to coalesce the inner and outer layers together at all points where they come in contact so that the polymer cocoon becomes unitary and non-delaminating. Preferably, the stent body itself is of limited axial extent, like a ring, or a series of spaced-apart rings, or else it possesses a number of apertures extending entirely through the stent at short axial spacing, so that the remaining spaces or apertures are covered over or bridged by both the inner and outer polymer layers, which coalesce into a continuous barrier. The apertures, which may comprise five to eighty percent or more of the surface area of the stent, constitute a grid or network of regions or tack points through which the material is coalesced and continuously bonded. When the stent is expanded, its changes in dimension and orientation may locally introduce shear which separates the stent or support body from the polymer. However, the support body is able to shift only within the regions where the inner and outer portions of the tube have not coalesced to each other, and thus it locally distributes strain to the surrounding polymer in a manner generally effective to prevent rupture and prevents the development of extended pockets or voids which could impair performance in use.

In embodiments where a two tube construction is cuffed and assembled to arrive at a similarly unitized and seamless stent. This is done as follows: first a tube of polymer is placed through the center of the stent and the ends of the tube are folded back over the stent for a short distance, or are expanded in radial extent and then folded back. Next, a second tube is placed over the outside of the stent covering the folded back ends of the first tube. As before, the assembly is then passed through an oven to shrink the outside and inside layers into unitary coalesced covering enclosing the entire stent, which is continuous and seamless over the end regions. One variation of this two-tube construction is to place the second tube over the stent before folding back the cuffs formed by the inner tube. In that case, the cuffs cover the ends of the second tube. The second tube may be a tube having different porosity than the first tube and may for example, have the node size of twenty to one hundred micrometers or more, and preferably thirty to sixty micrometers, which is suitable for ingrowth of surrounding tissue. This serves to better anchor the structure in the stented passage. Alternatively, both inside and outside polymer walls may have a relatively small pore size of one to five micrometers to provide a higher degree of isolation of the stent from surrounding tissue, or assure that tissue does not penetrate through the continuous boundary.

BRIEF DESCRIPTION OF THE DRAWINGS

These and other features of the invention will be understood from the description below taken together with drawings of representative embodiments and methods of practicing the invention, wherein.

DETAILED DESCRIPTION

Figures 1A, 1B, 1C:
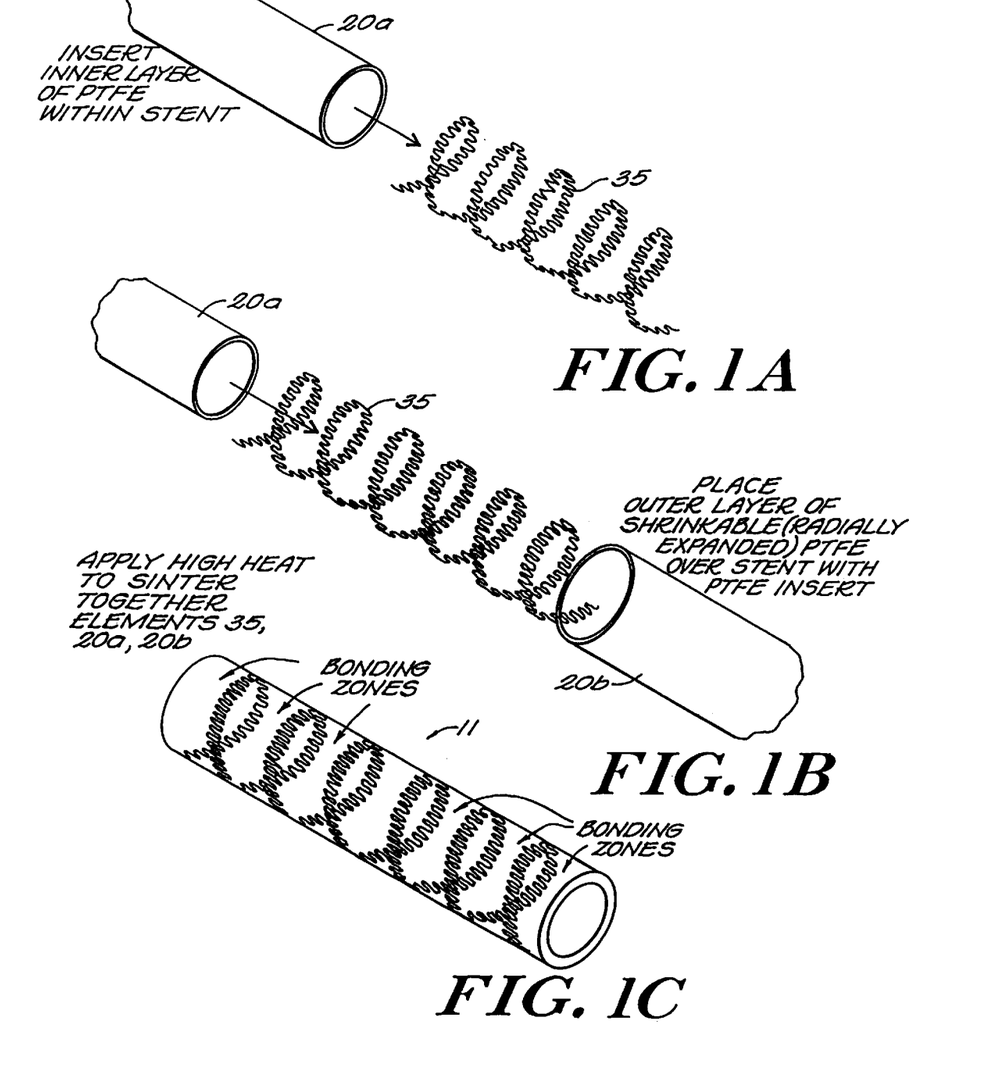
FIGS. 1A–1C schematically show a method of forming the enclosed stent of the present invention.

As shown in FIGS. 1A–1C, a method of forming an enclosed, protected support or reinforcing element 10 such as a stent includes the steps of (FIG. 1A) taking a first film-like body of liner material shown as a tube 20a, and placing it within a stent 30, and the step (FIG. 1B) of covering the assembly with an outer film of material, 20b. The entire assemblage is then heated together (FIG. 1C) so as to unitize the inside and outside layers with the stent 30 secured between them. The foregoing schematically represented method is preferably carried out with a material such as expanded polytetrafluoroethylene (PTFE) which has a porosity imparted by previous stretching or expansion of the material. In this case, at least the second or outer layer of the material is preferably a radially-expanded but unsintered layer, so that when it is heater it shrinks back toward its unexpanded state and presses against the inner layer. Further radial pressure may be provided to urge the inner and outer polymer layers together.

Figures 2A, 2B, 2C:
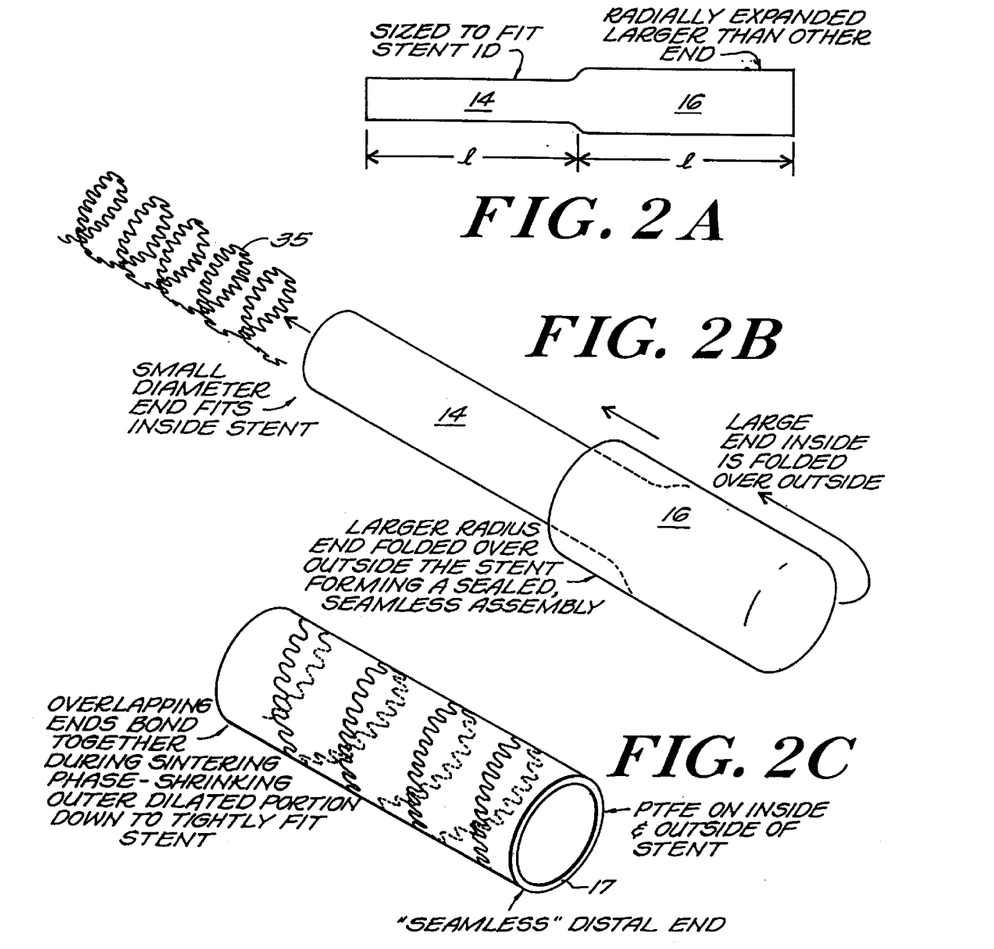
FIGS. 2A–2D illustrate a two-element unitized stent construction.
Figure 2D:
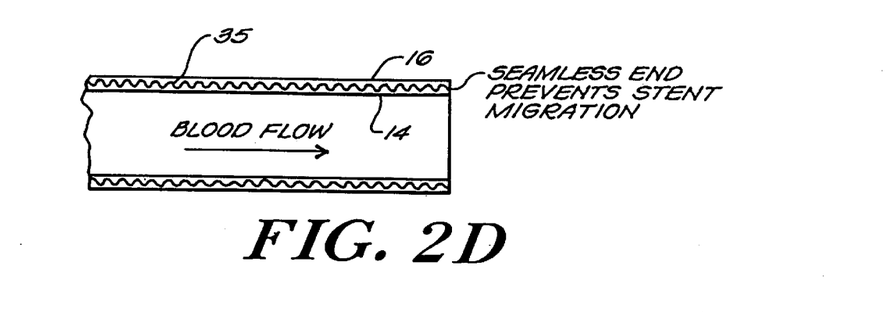

One preferred method of fabricating the structure schematically shown in FIGS. 1A–1C is illustrated in FIGS. 2A–2C. In accordance with this method, a tube of the polymer material 20 having a diameter d is provided. One end of the tube is expanded radially, for example by inserting an expandable balloon inside the tube and inflating it to increase the diameter of the tube by a factor of five to five hundred percent or more. This produces a stepped tube illustrated in FIG. 2A having a small diameter portion 14 of diameter d and a large diameter end 16 of diameter D>d, which may in addition have a greater degree of porosity. A stent 30 is then placed over the small end 14 and the large end 16 is folded back over the stent 30 (FIG. 2B). This forms a structure that is half the original tube length, with a single cuff resulting from the continuous fold of material 16 over the right hand end portion, as illustrated, of the device. Once folded over in this fashion to form an assembly half the length of the original tube, heat is applied to shrink the outside down in upon the inside, enclosing the stent 30 therebetween (FIG. 2C). An inflatable sleeve or tightly fitting form may clamp around the outside to provide an inwardly-directed, radial, pressure. FIG. 2D illustrates a cross section taken longitudinally of the resultant construction.

Figure 3A:
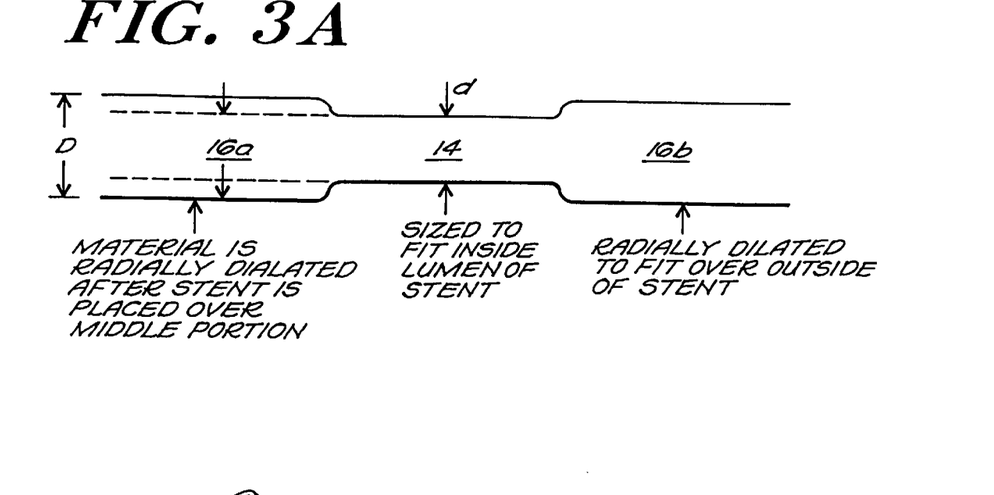
FIGS. 3A–3F illustrate another two element unitized construction and the method of making it.
Figure 3B:
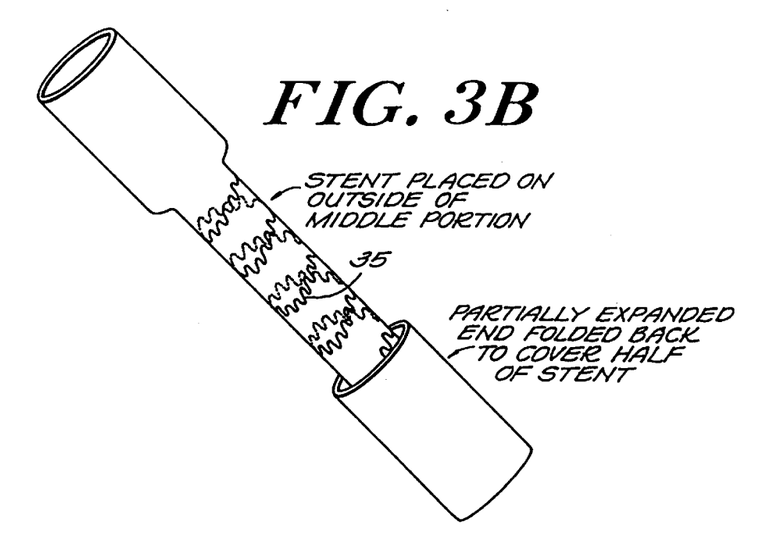
Figure 3C:
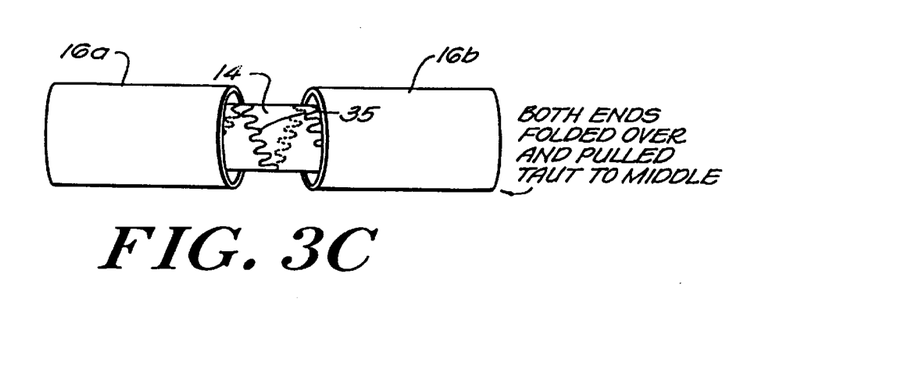
Figure 3D:
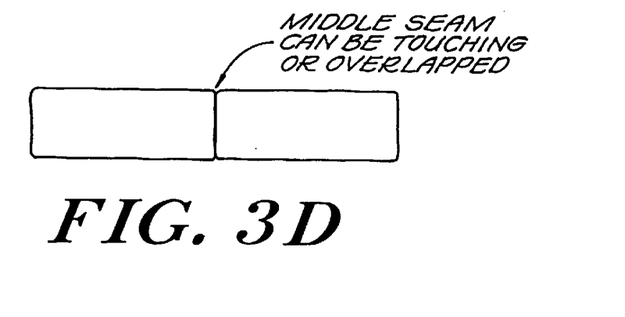
Figure 3E:
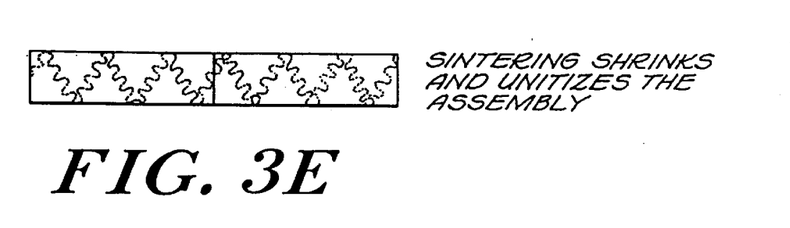
Figure 3F:
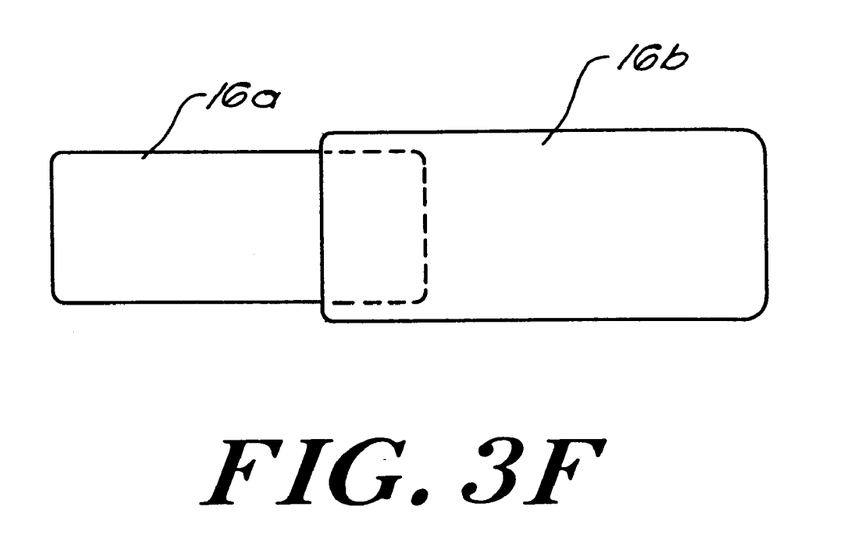

FIGS. 3A–3E show a further practice of the method of the present invention. In accordance with this method, a single tube of polymer material is provided as before, but both ends are inflated to form a first large diameter portion 16a that joins continuously with the uninflated central portion 14, which, in turn, extends to another end 16b which has also been inflated and enlarged. Preferably, the portion 14 extends for approximately half the length of the original tube while the portions 16a and 16b are each one quarter of the length of the tube length or slightly more. This tube may be placed over a mandrel (not shown) which provides a temporary rigid element to facilitate the process. As shown in FIG. 3B, the stent 30 is then placed around the central portion 14 and one end, illustrated as end 16b of the expanded tube, is folded back along the axial direction to cover a portion of the stent. As illustrated, the folded back end portion 16b extends roughly halfway along the tube length. As best seen in FIGS. 3C and 3D, the remaining end 16a is then folded and pulled taut to the middle. The ends can be touching as shown in FIGS. 3D, or they may be overlapped to provide a single seam in which one end slightly extends over the already double layer of the other end. The assembly then remains on the mandrel and is heated for a time sufficient to shrink both of the turned-over ends together down over the stent and to coalesce with the underlying material. With this construction, both ends of the stent are closed by a continuous smooth seamless cover, and both the inside and outside films are bonded to each other or coalesced with heat so that they form a nondelaminating and unitized cocoon around the stent.

in this construction, the stent body 30 itself may be a spiral-shaped zig-zag wire body which lies generally in the plane of the cylindrical surface on which it extends, and which when radially expanded places the bends under tension and draws the band of zig-zags slightly narrower and straighter, thus expanding in radius by elongating slightly along its spiral direction. Shear between the surrounding polymer layers and the wire stent material itself will thus naturally occur, but will be directed along the relatively narrow band in which the stent lies. The crimps themselves may be of very closely spaced zigs and zags which effectively prevent the outer film from contacting the inner film in the narrow band closely surrounding this area. With such a construction, the stent lies in a tunnel or pocket formed between the layers. Because the layers fit tightly, the support effectively transfers strain to the polymer. Thus breaking or rupture of the film does not occur as the stent expands. As noted above, a preferred material is an expanded polytetrafluoroethylene, which when heated shrinks back and coalesces with contacting portions of the polymer from the other side of the stent. The heating is carried out to not over sinter, so this material is also capable of restretching without rupture. Thus that both the stent and the surrounding polymer are expandable and may, for example, be placed by endovascular delivery and expansion in situ.

Figure 4A:
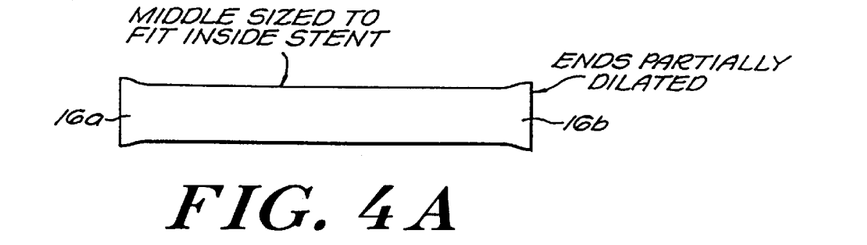
FIGS. 4A–4C show an embodiment with covered ends and a seamless interior and a method for making it.
Figure 4B:
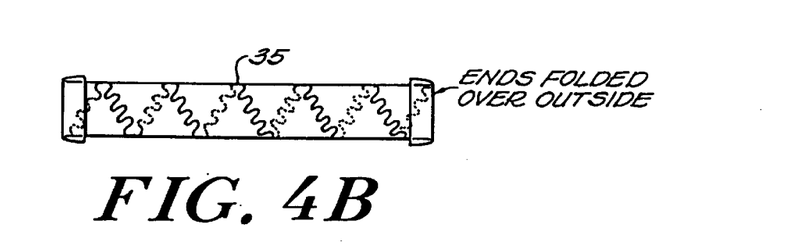
Figure 4C:
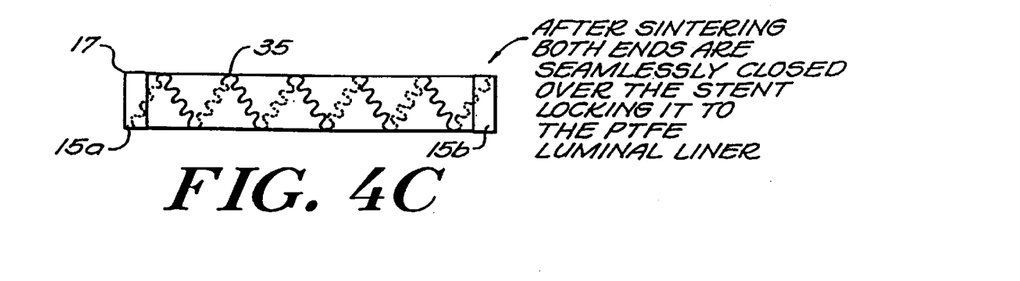

In addition to the foregoing methods of fabrication, the invention also contemplates a stent construction wherein the stent body has a continuous and seamless covering over ends of the stent and along the full length of the body, but the body covering extends only on one side, the inside or the outside, of the cylindrical stent. This is achieved as shown in FIGS. 4A–4C. In this embodiment of the invention, a tube 14 is expanded at each end, as before, to form expanded end portions 16a and 16b. However the end portions, 16a and 16b, are each of relatively short length, approximately one centimeter, and are folded back over the stent 30 only for a distance sufficient to cuff the ends and to provide a short band or margin approximately one half to one centimeter wide at the ends of the stent. As before, the assembly is then heated to shrink down the folded over material and unitize the cuffs thus formed at each end. In this embodiment as in the first described schematic treatment of the method, a tube may then be placed over the outside to cover the folded back portions. If such an outer tube is provided, it is constrained so that its ends extend beyond the edges of the folded back cuff portions and lie in the band indicated by 15a, 15b in the drawing. Heat is applied with the ends constrained so that the second tube shrinks radially but not axially and the cocoon structure extends and is maintained over the full length of the prosthesis. As in the previous embodiments, the closed ends are entirely seamless and the outer tube coalesces with the underlying material at a region away from the ends to form a continuous enclosing assembly for the stent.

Figure 5A:
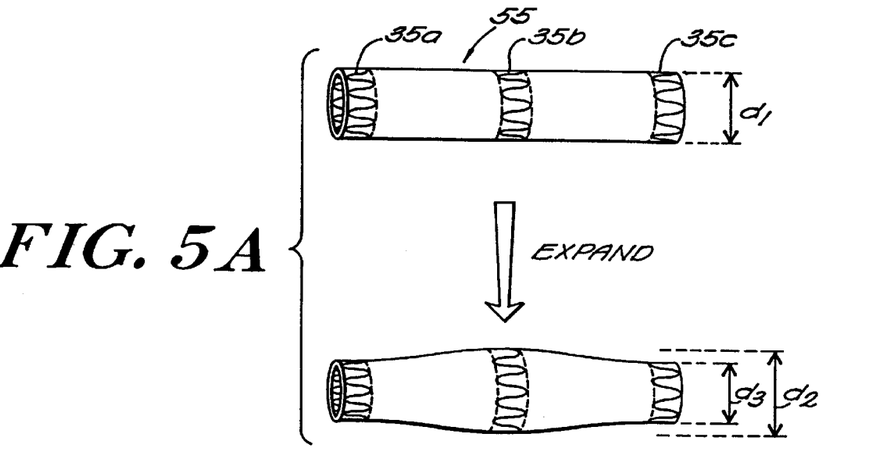
FIGS. 5A–5C show several non-uniform expansion embodiments.
Figure 5B:
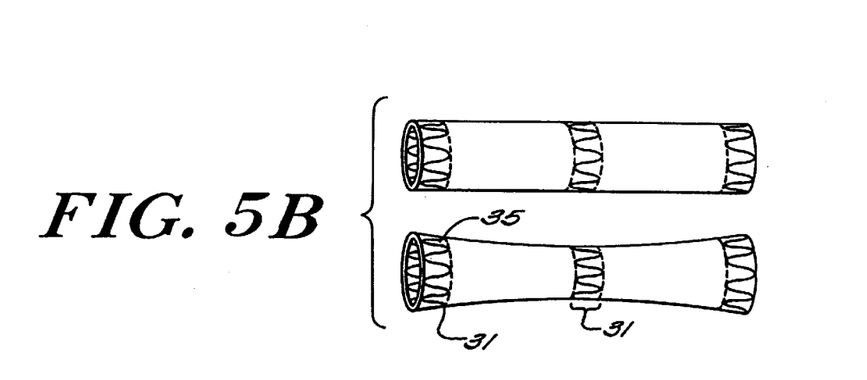

In accordance with another aspect of the present invention, a vessel support is fabricated with a structure to assume a radially-varying extent along its length when expanded, such that one or both ends thereof are larger than its center (as shown in FIG. 5A), or vice-versa (as shown in FIG. 5B).

As illustrated in FIG. 5A, a PTFE support liner or graft assembly 50 is fabricated having one or more expanding rings or stents 30a, 30c at its ends and one or more rings 30b centrally along its length, all having an initial diameter $d_1$. In this embodiment the end rings 30a, 30c are made of heavier gauge material, or are otherwise dimensioned so that they either are more resistant to expansion, or else have a limited net expanded size $d_2$. The central rings 30b are either more easily expanded (lower resistance) or are dimensioned so that they expand to a larger diameter $d_3$. The result is that during expansion the support assembly 50 assumes a shape which bulges out in the center. This shape aides in preventing the inflation balloon from slipping out of the support during the inflation process, which may require several cycles of balloon expansion to expand successive lengths of the support tube. This contour also enables the support to conform more closely to a region of vessel having an aneurysm or bulge.

FIG. 5B illustrates a related construction in which the end rings have a lesser resistance to expansion or a larger net expanded diameter than the center rings. In this case the intermediate and/or final expanded size is greater at the ends, creating flared or trumpet-shaped ends or a venturi-like profile. This profile is intended to assure a smooth transition from the unsupported vessel lumen to the prosthesis, without projecting edges at the prosthesis ends. Each of the narrow rings 30 may reside in a pocket or band 31 such that expansion occurs relatively freely and some motion of the stent may occur between the inner and outer surfaces without impairing continuity of the PTFE envelope material.

Figure 5C:
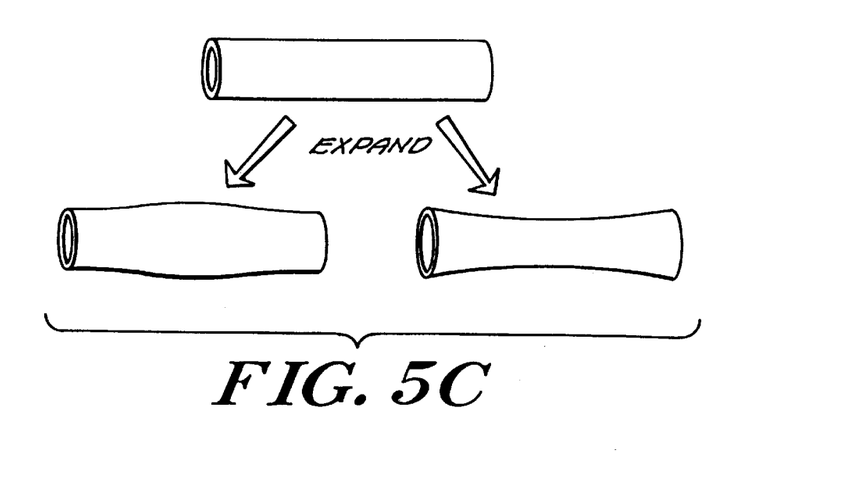

A related construction, applicable to either bulge- or flare-expansion contours is shown in FIG. 5C. This figure shows a PTFE body which has been formed with an inner region, a middle region and an outer region, as described for example in the above-mentioned patent application entitle PROSTHESIS WITH IN-WALL MODULATION. That construction, instead of enclosing stent or rings 30, surrounds a separate tube, wrapping or body of fluoropolymer material, in the region between the outer and inner surface portions in a unitary coalesced assembly. In this case, when constructing the assembly as shown in FIG. 5C without a stiff stent or support member between the inner and outer surfaces, the degree of expansion of the assembly may be varied by providing the prosthesis with a different degree of sintering at different points along the length of the prosthesis. This may be done as described further below, by feeding the assembly end-first into a sintering oven at a controlled rate to sinter each end more than the center. This provides grater tensile strength of the material at both ends, and results in a bulged prosthesis when expanded, as shown at the left of the figure. The opposite distribution may be provided by reciprocating the assembly while it is centrally positioned in a short oven such that each end sticks out of the heat zone for a substantial portion of the sintering cycle, to result in flared-end expansion material at the end portions having lower tensile strength.

Thus, the invention further provides expandable vessel liners or supports having radial taper or curvature along their length.

EXAMPLE 1

The following example describes the construction of a solid tube of PTFE having a radially expandable stent within the tube. A starting tube, or substrate, was a substantially uniform length of axially-stretched tubing formed by extrusion as described, for example, in U.S. Pat. Nos. 5,433,909 and 5,474,824. The PTFE substrate was a uniaxially-oriented tube having nodes interconnected by fibrils oriented substantially in a single longitudinal direction. The fibrils were approximately 30 μm in length. The PTFE substrate had an internal diameter of 2.5 mm and a wall thickness of approximately 0.25 mm.

This PTFE substrate material was placed on a stainless steel mandrel having a diameter of 2.7 mm. Thus, a small amount of radial expansion was required to get the material on the mandrel. A Cordis peripheral stent (part number 2969363) was placed over PTFE layer, and a second PTFE layer was placed covering the stent. The second layer consisted of the PTFE substrate material described above, expanded to 4 mm by sliding the material over a stainless steel mandrel with a diameter of 4 mm to radially expand it. After radial expansion, the PTFE material moved freely over the stent. The PTFE/stent/PTFE combination was secured at both ends to prevent slippage along the mandrel, and the combination was placed in an oven and sintered at 360° C. for a 15 minute time period. During sintering, the outer layer of PTFE recovered to it original diameter and attached to the inner layer of PTFE. The assembly was removed from the oven and the excess PTFE was removed. The resulting structure contained the stent entirely enveloped within a closed body of PTFE.

The PTFE stent combination was expanded with a Blue Max balloon dilation catheter with a balloon O.D. of 9 mm and a balloon length of 4 cm. Using multiple inflations the stent combination was expanded along its entire length.

EXAMPLE 2

The following example describes the construction of a solid tube of PTFE having a radially expandable stent within the tube, and wherein a single piece of PTFE tubing is used to construct the stent combination.

The PTFE substrate was the same uniaxially-oriented tube as that of Example 1, having nodes interconnected by fibrils oriented substantially in a single longitudinal direction. The fibrils were approximately 30 μm in length, and the PTFE substrate has an internal diameter of 2.5 mm and a wall thickness of approximately 0.25 mm. Half the length of the PTFE tube was expanded to 6 mm by sliding the tube material over a mandrel having a diameter of 6 mm. FIG. 2A depicts what the PTFE tube looks like after this processing step. The small portion of the PTFE tube was then placed on a stainless steel mandrel having a diameter of 2.7 mm. Thus, a small amount of radial expansion was required to get the material on the mandrel. A Cordis peripheral stent (part number 2969363) was placed over the PTFE layer. Next, the expanded end of the PTFE tube was folded back to cover the stent. The PTFE material moved freely over the stent, and the PTFE and stent combination was secured at both ends to prevent slippage along the mandrel. The combination was placed in an over and sintered at 360° C. for a 15 minute time period. During sintering, the outer layer of the PTFE recovered to its original diameter and attached to the inner layer of PTFE.

The PTFE and stent combination was removed from the oven and excess PTFE was trimmed.

The PTFE stent device produced in this fashion was expanded with a Blue Max balloon dilatation catheter with a balloon O.D. of 9 mm and a balloon length of 4 cm. Multiple inflations were used to expand the stent combination along its entire length.

EXAMPLE 3

The following example describes the construction of a solid tube of PTFE having a plurality of spaced apart radially expandable stents within the tube.

The starting PTFE substrate was an uniaxially-oriented tube having nodes interconnected by fibrils oriented substantially in a single longitudinal direction. The fibrils was approximately 30 μm in length. The PTFE substrate had an internal diameter of 2.5 mm and a wall thickness of approximately 0.25 mm.

A layer of this PTFE material was placed on a stainless steel mandrel having a diameter of 2.7 mm. Thus, a small amount of radial expansion was required to get the material on the mandrel. Two Palmaz stents (part number P394) were placed over the PTFE layer. The stents were spaced apart approximately 4 cm. The PTFE material described above was expanded to 4 mm by sliding the material over a stainless steel mandrel with a diameter of 4 mm and the expanded tube was placed over the stents. The radially expanded PTFE material moved freely over the stents. The PTFE and stent combination was secured at both ends to prevent slippage along the mandrel. The combination was placed in an oven and sintered at 360° C. for a 15 minute time period. During sintering, the outer layer of PTFE recovered to its original diameter and attached to the inner layer of PTFE. The PTFE and stent combination was removed from the oven and excess PTFE was removed.

The PTFE stent combination was expanded with a Blue Max balloon dilatation catheter with a balloon O.D. of 9 mm and a balloon length of 4 cm. Multiple inflations were used to expand the stent combination along its entire length.

EXAMPLE 4

The starting PTFE substrate was made from a uniaxially-oriented tube having nodes interconnected by fibrils oriented substantially in a single longitudinal direction. The PTFE substrate was 60 cm in length had an internal diameter of 6 mm, with a wall thickness of approximately 0.6 mm and an average internodal distance of 60 μm on the exterior surface and 20 μm on the interior surface. The tube material was marked 1 cm increments along the length of the tube.

This graft material was placed on a stainless steel mandrel having a diameter of 6 mm which allowed for the free movement of the graft along the length of the mandrel. The graft/mandrel combination was then fed along its long axis into and oven set at 360° C. at a rate of 0.1 cm/sec. Consequently, the portion of the tube entering the oven initially is subjected to a longer sintering time than other portions of the tube. The tube was not restrained during sintering which permitted longitudinal contraction, which is also referred to as free sintering. Free sintering results in a reduction in the internodal distance.

Samples of the tube were taken at points 12.5, 22.5 and 52.5 centimeters along the longitudinal axis. Thus, the samples had been subjected to different free sintering times. Scanning electron micrographs (SEMs) were made to observe the effect of sintering on the PTFE material.

EXAMPLE 5

An expanded PTFE tube was made with variable porosity characteristics. The PTFE substrate was made from a uniaxially-oriented tube having node interconnected by fibrils oriented substantially in a single longitudinal direction. The PTFE substrate was 100 cm in length has an internal diameter 6 mm, a wall thickness of approximately 0.45 mm and an average internodal distance of 60 $\mu$m on the exterior surface and 20 $\mu$m on the interior surface. The tube as marked in 0.5 mm increments along the length of the tube.

The graft was placed on a stainless steel mandrel having a diameter of 6 mm which allowed for the free movement of the graft along the length of the mandrel. The graft mandrel combination was then fed along its long axis into an oven set of 320° C. at a rate of 0.05 cm/sec to the 50 cm position. Consequently, the portion of the tube entering the oven initially was subjected to a longer sintering time than other portions of the tube. The tube was not restrained during sintering, which permitted longitudinal contraction. This is referred to as free sintering. Free sintering results in a reduction in the internodal distance. The tube mandrel combination was rotated 180°. The graft mandrel combination was then fed along its long axis into an oven set at 320° C. at a rate of 0.05 cm/sec to the 50 cm position. This permitted the free sintering of the opposite section of tube material in a similar fashion to the initial section. Thus, the center portion of the tube was subjected to the shortest period of free sintering.

Samples of the tube material were taken at various positions along the longitudinal axis and subjected to radial tensile strength, foreshortening, and internodal distance measurements, and the radial tensile strength was found to be directly related to the foreshortening percentage and internodal distance.

The foregoing constructions and methods provide new and useful constructions of stent sand other solid or springy support with a cover or surrounding of PTFE material. This cover is permanently attached and closely conforms, providing a surface biocompatibility and a continuous surface that is capable of expansion while retaining it integrity, and which essentially avoids end—or flow-surface seams or irregularities. The invention being thus disclosed and described, variations and modifications will occur to those skilled in the art, and such variations and modifications are considered to be within the scope of the invention, as set forth in the claims appended herein.

We claim:

1. A method of fabricating a stent, comprising the steps of:
    positioning a tube formed of radially expandable polymer centrally in a stent body,
    radially expanding a first portion of the tube,
    folding back the radially expanded first portion of the tube over a second portion of the tube so the tube extends inside and outside the stent body and forms a cuff seamlessly and continuously enclosing at least one end of the stent body within a cocoon, and
    coalescing the tube to seal the stent body within the cocoon.

2. The method of claim 1, wherein the step of coalescing includes a step of heating a contract and join the tube to the stent body.

3. The method of claim 1, including the step of increasing porosity of the radially expanded first portion of the tube.

4. A method of fabricating a stent, comprising the steps of;
    positioning a tube formed of radially expandable polymer within a stent body, the tube having a first end and a second end,
    folding the first end of the tube over a first end of the stent body to form a first cuff enclosing the first end of the stent body within a cocoon,
    folding the second end of the tube over a second end of the stent body to form a second cuff enclosing the second end of the stent body within a cocoon, and
    coalescing the tube to seal the first end of the stent body within the first cuff and the second end of the stent body within the second cuff.

5. The method of claim 4, wherein the step of coalescing includes the step of heating to contract and join the tube to the stent body.

6. The method of claim 4, further comprising the step of increasing porosity of the first end of the tube.

7. The method of claim 4, wherein the step of folding the first end includes the step of extending the first cuff to the middle of the tube.

8. The method of claim 7, wherein the step of folding the second end includes the step of extending the second cuff to the middle of the tube adjacent the first cuff to form a middle seam therebetween.

9. The method of claim 7, wherein the step of folding the second end includes the step of extending the second cuff over the first cuff.

10. A stent comprising:
    a radially expandable member, and
    A polymer tube having first and second ends, a portion of the polymer tube being positioned within the radially expandable member, the first end of the polymer tube being folded over a first end of the radially expandable member to form a first cuff, the second end of the polymer tube being folded over a second end of the radially expandable member to form a second cuff, wherein the second cuff overlaps the first cuff.

11. The stent of claim 10, wherein the first end of the polymer tube has a porosity greater than the porosity of the portion of the polymer tube positioned within the radially expandable member.

12. The stent of claim 10, wherein the first and second ends of the polymer tube have a porosity greater than the porosity of the portion of the polymer tube positioned within the radially expandable member.

13. The stent of claim 10, wherein the polymeric tube is constructed from polytetrafluoroethylene (PTFE).

14. The stent of claim 10, wherein the radially expandable member comprises a spiral-shaped, zig-zag wire body.

15. The stent of claim 10, wherein the radially expandable member comprises a plurality of spaced-apart expansion rings.

16. An expandable vessel support comprising:
    a tube of polymeric material having first and second ends,
    a first expansion ring positioned at the first end of the tube,
    a second expansion ring position at the second end of the tube, and
    a third expansion ring positioned between the first and second ends, the third expansion ring being expandable to a greater diameter than the first and second expansion rings.

17. The expandable vessel support of claim 16, wherein the first and second expansion rings are constructed from a heavier gauge material than the third expansion ring.

18. The expandable vessel support of claim 16, wherein the expansion rings are positioned within pockets formed in the tube of polymeric material.

19. The expandable vessel support of claim 16, wherein the polymeric material is PTFE.

20. An expandable vessel support comprising:
    a tube of polymeric material having first and second ends,
    a first expansion ring positioned at the first end of the tube, a second expansion ring position at the second end of the tube, and a third expansion ring positioned between the first and second ends, the first and second expansion rings being expandable to a greater diameter than the third expansion ring.

21. The vessel support of claim 20, wherein the third expansion ring is constructed from a heavier gauge material than the first and second expansion rings.

22. The vessel support of claim 20, wherein the expansion rings are positioned within pockets formed in the tube of polymeric material.

23. The vessel support of claim 20, wherein the polymeric material is PTFE.

24. An expandable vessel support comprising:

a tube of polymeric material having a first end and a second end, the first and second ends being constructed to have greater radial tensile strength than a portion of the tube between the first and second ends to permit increased expansion of the portion of the tube between the first and second ends, the tube having a radially tapered configuration when expanded.

25. The vessel support of claim 24, wherein the polymeric material is PTFE.

26. An expandable vessel support comprising:

a tube of polymeric material having a first end and a second end, the first and second ends being constructed to have less radial tensile strength than a portion of the tube between the first and second ends to permit increased expansion of the first and second ends, the tube having a radially tapered configuration when expanded.

27. The vessel support of claim 24, wherein the polymeric material is PTFE.

28. A method of fabricating an expandable vessel support having a radially tapered configuration when expanded, the method comprising the steps of:

forming a tube of polymeric material having a first and a second end, sintering the first and second ends of the tube for a time period longer than a portion of the tube between the first and second ends to increase the radial tensile strength of the first and second ends and provide a radially tapered configuration to the tube when expanded.

29. The method of claim 28, wherein step of sintering occurs without restraining the tube.

30. A method of fabricating an expandable vessel support having a radially tapered configuration when expanded, the method comprising the steps of:

forming a tube of polymeric material having a first and a second end, sintering the first and second ends of the tube for a time period shorter than a portion of the tube between the first and second ends to reduce the radial tensile strength of the first and second ends and provide a radially tapered configuration to the tube when expanded.

31. The method of claim 30, wherein step of sintering occurs without restraining the tube.

* * * * *